(12) United States Patent
Choo et al.

(10) Patent No.: US 10,426,341 B2
(45) Date of Patent: *Oct. 1, 2019

(54) SYSTEMS AND METHODS FOR SENSING INTRAOCULAR PRESSURE

(71) Applicants: CALIFORNIA INSTITUTE OF TECHNOLOGY, Pasadena, CA (US); THE REGENTS OF THE UNIVERSITY OF CALIFORNIA, Oakland, CA (US)

(72) Inventors: Hyuck Choo, Pasadena, CA (US); David Sretavan, San Francisco, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/868,219

(22) Filed: Sep. 28, 2015

(65) Prior Publication Data

US 2016/0015266 A1 Jan. 21, 2016

Related U.S. Application Data

(62) Division of application No. 13/717,324, filed on Dec. 17, 2012, now Pat. No. 9,173,564.

(Continued)

(51) Int. Cl.
*A61B 3/16* (2006.01)
*B82Y 15/00* (2011.01)
(Continued)

(52) U.S. Cl.
CPC .............. *A61B 3/16* (2013.01); *B82Y 15/00* (2013.01); *G01L 1/247* (2013.01); *G01L 9/0077* (2013.01); *B82Y 5/00* (2013.01)

(58) Field of Classification Search
CPC .. B82Y 5/00; B82Y 15/00; A61B 3/16; A61B 3/165; A61B 3/18; A61B 3/185;
(Continued)

(56) References Cited

U.S. PATENT DOCUMENTS 5,005,577 A   4/1991   Frenkel
5,830,139 A   11/1998  Abreu
(Continued)

FOREIGN PATENT DOCUMENTS

| WO | WO 2013/059195 A1 | 4/2013 |
|----|-------------------|--------|
| WO | WO PCT/US2012/070047 | 4/2013 |
| WO | WO PCT/US2012/070047 | 6/2014 |

OTHER PUBLICATIONS

EP, 12858598.1 Supplementary Search Report, dated Apr. 22, 2015.
(Continued)

*Primary Examiner* — David J. McCrosky
(74) *Attorney, Agent, or Firm* — One LLP

(57) ABSTRACT

Systems and methods of sensing intraocular pressure are described. An example miniaturized intraocular pressure (IOP) monitoring system is provided using a nanophotonics-based implantable IOP sensor with remote optical readout that can be adapted for both patient and research use. A handheld detector optically excites the pressure-sensitive nanophotonic structure of the IOP-sensing implant placed in the anterior chamber and detects the reflected light, whose optical signature changes as a function of IOP. Optical detection eliminates the need for large, complex LC structures and simplifies sensor design. The use of nanophotonic components improves the sensor's resolution and sensitivity, increases optical readout distance, and reduces its size by a factor of 10-30 over previous implants. Its small size and (Continued)

convenient optical readout allows frequent and accurate self-tracking of IOP by patients in home settings.

25 Claims, 17 Drawing Sheets

Related U.S. Application Data

(60) Provisional application No. 61/601,464, filed on Feb. 21, 2012, provisional application No. 61/576,493, filed on Dec. 16, 2011.

(51) Int. Cl.
*G01L 9/00* (2006.01)
*G01L 1/24* (2006.01)
*B82Y 5/00* (2011.01)

(58) Field of Classification Search
CPC .. A61B 5/0002; A61F 9/00781; A61F 9/0017; G01L 1/247; G01L 9/0077
See application file for complete search history.

(56) References Cited

U.S. PATENT DOCUMENTS

| | | | |
|---|---|---|---|
| 6,710,355 B2 | 3/2004 | Youngner | |
| 9,173,564 B2 * | 11/2015 | Choo | A61B 3/16 |
| 9,226,856 B2 | 1/2016 | Walsh et al. | |
| 9,671,301 B2 | 6/2017 | Carroll et al. | |
| 2003/0078487 A1 | 4/2003 | Jeffries et al. | |
| 2004/0039297 A1 | 2/2004 | Abreu | |
| 2004/0087849 A1 | 5/2004 | Masaki | |
| 2004/0254438 A1 | 12/2004 | Chuck et al. | |
| 2007/0112263 A1 | 5/2007 | Fink et al. | |
| 2007/0156079 A1 | 7/2007 | Brown | |
| 2008/0226217 A1 | 9/2008 | Kilic et al. | |
| 2009/0030300 A1 | 1/2009 | Ghaboussi et al. | |
| 2009/0076367 A1 | 3/2009 | Sit et al. | |
| 2009/0099442 A1 | 4/2009 | Paden et al. | |
| 2010/0053608 A1 | 3/2010 | Lee | |
| 2010/0094164 A1 | 4/2010 | Chronis | |
| 2010/0286498 A1 | 11/2010 | Dacquay et al. | |
| 2011/0081109 A1 | 4/2011 | Thylen et al. | |
| 2011/0160561 A1 | 6/2011 | Hastings et al. | |
| 2012/0041552 A1 | 2/2012 | Chuck et al. | |
| 2012/0302862 A1 | 11/2012 | Yun et al. | |
| 2012/0329935 A1 | 12/2012 | Matsumura et al. | |
| 2013/0165762 A1 | 6/2013 | Choo et al. | |
| 2015/0157453 A1 | 6/2015 | Nazinzadeh et al. | |

OTHER PUBLICATIONS

Chen et al. "Wireless Intraocular Pressure Sensing Using Microfabricated Minimally Invasive Flexible-Coiled LC Sensor Implant," Journal of Microelectromechanical Systems, vol. 19, No. 4, pp. 721-734, Aug. 2010.

Photonic. Dictionary.com. Dictionary.com Unabridged. Random House, Inc. http://dictionary.reference.com/browse/photonic (accessed: Aug. 20, 2014).

N.G. Khlebtsov, et al., "Optical properties and biomedical applications of plasmonic nanoparticles", Journal of Quantitative Spectroscopy & Radiative Transfer 111 (2010) pp. 1-35.

M. Himmelhaus, et al., "Cap-shaped gold nanoparticles for an optical biosensor", Sensors and Actuators B 63 (2000) pp. 24-30.

Internet Archive Wayback Machine, "Why Parylene?", Parylene Engineering, May 3, 2009, retrieved from <https://web.archive.org/web/20090503080145/http://www.paryleneengineering.com/why_use_parylene.html> on Aug. 20, 2014.

EP, 12858598.1 Communication, dated Jan. 9, 2019.

Lu, G., et al., "Fabry-Perot type sensor with surface plasmon resonance", Applied Physics Letters, 2006, vol. 89, pp. 223904-1-223904-3.

\* cited by examiner

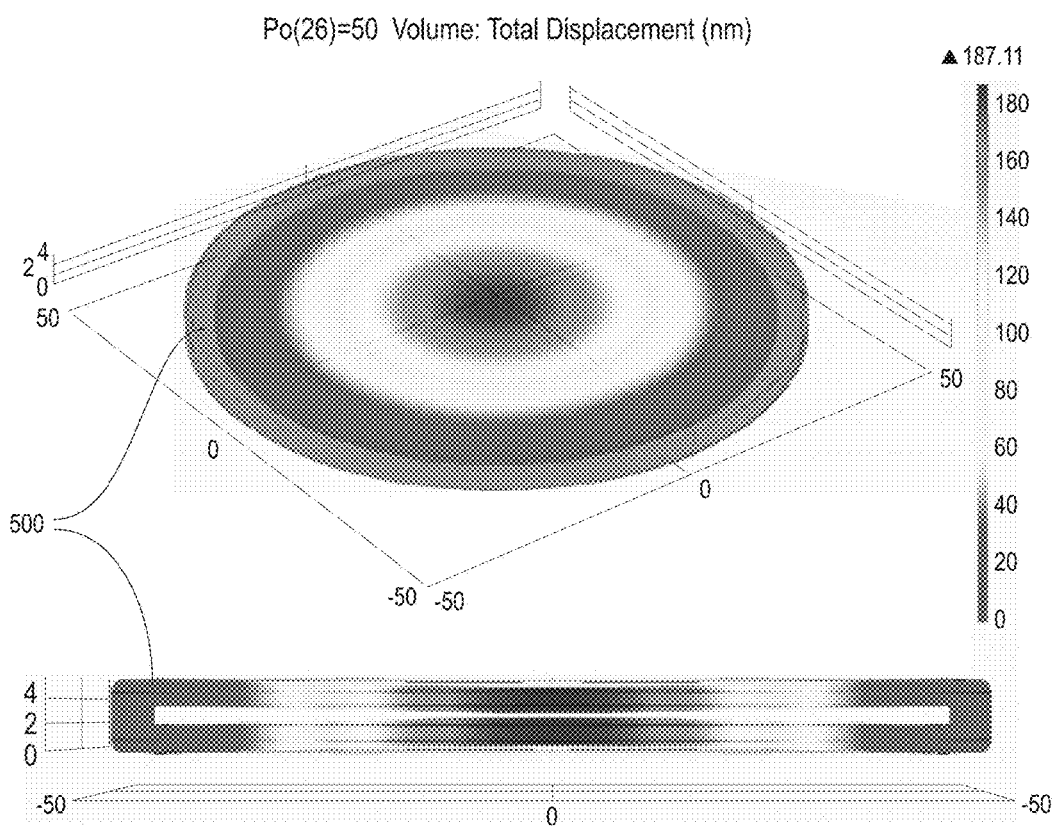

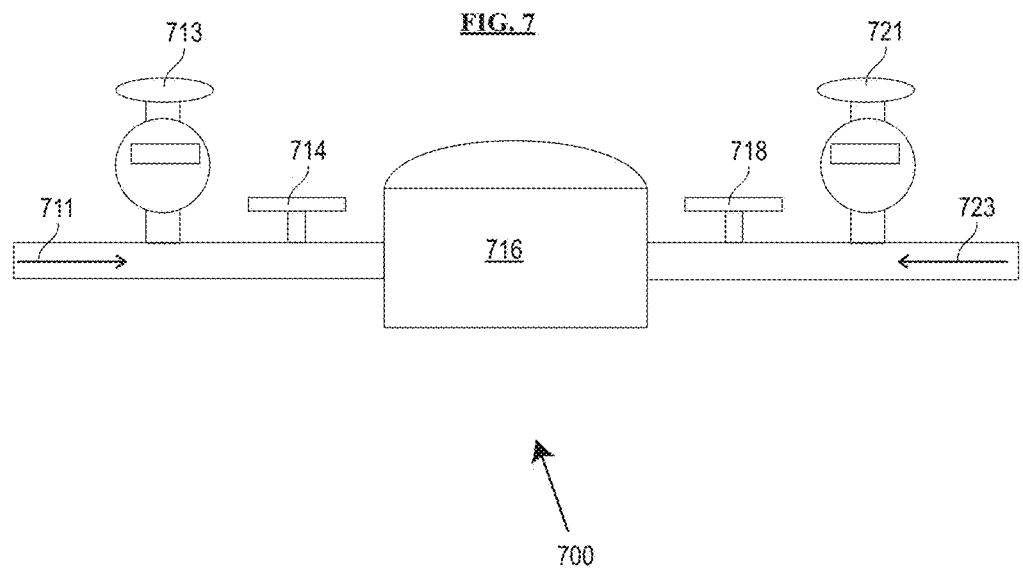

SYSTEMS AND METHODS FOR SENSING INTRAOCULAR PRESSURE

CROSS-REFERENCE TO RELATED APPLICATIONS

This application is a divisional of U.S. patent application Ser. No. 13/717,324, filed Dec. 17, 2012, which claims priority to U.S. Provisional Patent Application Ser. No. 61/576,493, filed Dec. 16, 2011, and U.S. Provisional Patent Application Ser. No. 61/601,464, filed Feb. 21, 2012, all of which are incorporated by reference herein in their entirety and for all purposes.

BACKGROUND OF THE INVENTION

Field of the Invention

The present invention relates generally to optical sensors, and in particular, to a system and method for sensing intraocular pressure.

Description of Related Art

Glaucoma is a leading cause of blindness, affecting an estimated four million Americans and seventy million individuals globally. As glaucoma typically affects the elderly, the aging demographic trends indicate that this disease will continue to be an ever-increasing socioeconomic burden to society. Elevated intraocular pressure ("IOP") is a major risk factor for glaucoma, and IOP monitoring is the single most important clinical management tool.

Despite the pervasive use of IOP readings for disease monitoring and the clinically proven importance of the aggressive lowering of IOP, current clinical management is primarily based on only periodic snapshots of IOP in the doctor's office obtained every few months. The inability of patients to easily monitor their own IOPs at different times of the day or during various daily activities hinders the comprehensive understanding of the IOP profile of individual patients and the possibility of custom-tailored IOP control.

In addition to its use as a patient monitoring parameter, IOP is also the standard readout used in glaucoma research. However, achieving an acceptable level of accuracy and repeatability in animal IOP measurements requires anesthesia and extreme care. Conducting such time-consuming measurements in large populations of animals is a major hurdle in glaucoma drug discovery.

The need for better IOP monitoring in clinical ophthalmology and in disease research has been widely appreciated. Existing measurement techniques in clinical use measure IOP indirectly. Current IOP measurements involve a form of contact or noncontact applanation tonometry. However, both modalities have difficulties in providing reliable and repeatable readouts of actual IOP values inside the eye. All tonometers produce indirect IOP readings by deforming the ocular globe and correlating this deformation to the pressure within the eye. Their readouts are heavily influenced by the corneal curvature and thickness, or corneal mechanical properties that vary due to co-existing ocular pathologies. For example, patients who have received laser photorefractive keratectomy have thinner corneas in the treated eyes and consistently show lower IOP when measured using tonometry techniques.

Tonometry currently requires specialized equipment operated by an ophthalmologist, optometrist, or skilled technician. Hence, IOP measurements are made typically in a doctor's office about two to four times per year. Since studies show that IOP varies widely throughout the day, quarterly measurements are poor representations of a patient's actual IOP profile.

A number of efforts have also been made to develop MEMS-based implantable IOP sensors with telemetric sensing. Unfortunately, the operating principle of this device puts a limit on the miniaturization of the sensor. Either the size of the sensor has to become large to achieve a longer transmission distance, or small devices lead to extremely short readout distances limit the practical use of the device. For example, to read IOP at a 2 centimeter distance, the IOP sensor has to be at least around 3 millimeters in size, which is too large in terms of patient acceptance and interference with ocular function.

The identification of new therapeutic compounds for glaucoma treatment utilizes IOP reduction in research animals as a screening parameter. Unfortunately, IOP measurements in animals using tonometry require anesthesia and extreme care for repeatability. Previously developed MEMS-based sensors are too large for use in rodent models, which make up more than 90% of the animal species used in glaucoma research. For example, these implants may range in size from 1-3 mm and are difficult to use in rodents that have corneal diameters of about 3.5 mm.

SUMMARY OF THE INVENTION

The above-described systems proposed a variety of techniques for measuring and monitoring intraocular pressure ("IOP"). However, there still exists a need for a highly miniaturized IOP monitoring system that can be adapted for both patient and research use. There also exists an unfulfilled need for a simple method to monitor IOP on a frequent basis at home, with easy, remote readout.

In view of the foregoing, one aspect of the present invention provides the first engineered nanophotonics sensor for biological pressure sensing. Nanophotonic components reduce the size of the sensors, as well as improve the sensitivity and strength of the readout signals. Embodiments of the invention provide a highly miniaturized IOP monitoring system using a nanophotonics-based implantable IOP sensor with remote optical readout that can be adapted for both patient and research use. A handheld detector optically excites the pressure-sensitive nanophotonic structure of the IOP-sensing implant placed in the anterior chamber and detects the reflected light, whose optical signature changes as a function of IOP. Optical detection eliminates the need for large, complex inductive-coupling/capacitive-sensing (LC) structures and simplifies sensor design. The use of precisely engineered nanophotonic components improves the sensor's resolution and sensitivity, increases optical readout distance, and reduces its size by a factor of 10-30 over previously reported implants. Its small size and convenient optical readout allows more frequent and accurate self-tracking of IOP by patients in home settings. In addition, this technology can be adapted for use in monitoring large cohorts of animals to support glaucoma research and drug discovery.

Thus, according to embodiments of the present invention, automated and systematic monitoring of IOP profiles can be achieved. This leads to better definition of IOP fluctuations, that when combined with aggressive lowering of IOP, results in better clinical outcome. It allows physicians to improve patients' adherence to medication and detect suboptimal IOP control. It also provides more accurate IOP profiles for individually tailored pressure-lowering treatment, and improves understanding of the relationship between IOP and disease. With adaptation, it also allows convenient IOP monitoring in large groups of research animals to accelerated fundamental discovery and drug development.

In view of the foregoing, one aspect of the present invention provides a method for sensing pressure, such as intraocular pressure. The method comprises establishing a gap between first and second membranes at a first pressure, the first and second membranes comprising nanophotonic components; transmitting a beam of light to the nanophotonic components; measuring a first reflectance of light off of the nanophotonic components at the first pressure; changing the gap between first and second membranes in response to a second pressure; transmitting the beam of light to the nanophotonic components; measuring a second reflectance of the light off of the nanophotonic components at the second pressure; and calculating the second pressure using the difference between the first reflectance of the light and the second reflectance of the light.

A device for sensing pressure, such as intraocular pressure, is also provided according to an embodiment of the invention. The device comprises first and second membranes separated by a gap, the first and second membranes being configured to move with respect to each other in response to changes in pressure; and a plurality of nanophotonic components embedded in the first and second membranes, the nanophotonic components being configured to reflect light. A system for sensing pressure, such as intraocular pressure, is further provided according to an embodiment of the invention. The system comprises a device configured to be implanted in an eye, the device comprising first and second membranes separated by a gap, the first and second membranes being configured to move with respect to each other in response to changes in pressure, and a plurality of nanophotonic components embedded in the first and second membranes, the nanophotonic components being configured to reflect light; and a reader configured to transmit light to the nanophotonic components and receive light reflected off of the nanophotonic components.

Still other aspects, features and advantages of the present invention are readily apparent from the following detailed description, simply by illustrating a number of exemplary embodiments and implementations, including the best mode contemplated for carrying out the present invention. The present invention also is capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 5B illustrates COMSOL simulation results of a sealed bilayer-membrane disk at maximum deformation of the membranes according to an embodiment of the invention.

FIG. 7 is a schematic diagram of an on-bench characterization chamber for characterizing a system for sensing intraocular pressure according to an embodiment of the invention.

DETAILED DESCRIPTION

Systems and methods for sensing intraocular pressure ("IOP") are described. In the following description, for purposes of explanation, numerous specific details are set forth in order to provide a thorough understanding of the exemplary embodiments. It is apparent to one skilled in the art, however, that the present invention can be practiced without these specific details or with an equivalent arrangement.

Figure 1A:
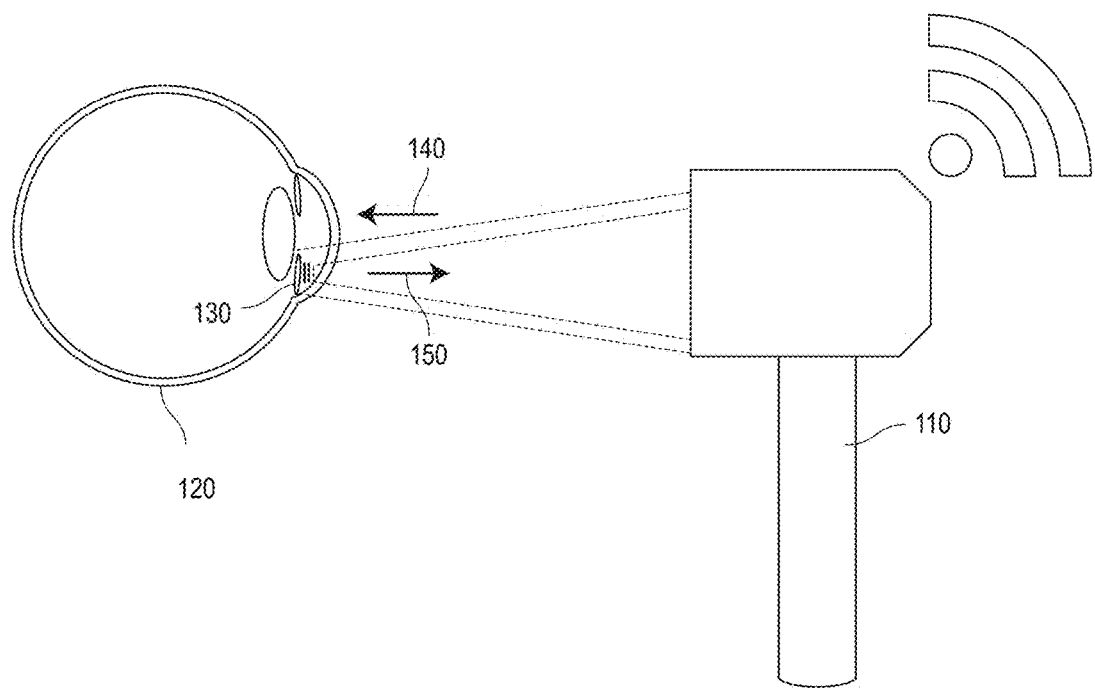
FIG. 1A is a schematic diagram of a system for sensing intraocular pressure in accordance with an embodiment of the invention.
Figure 1B:
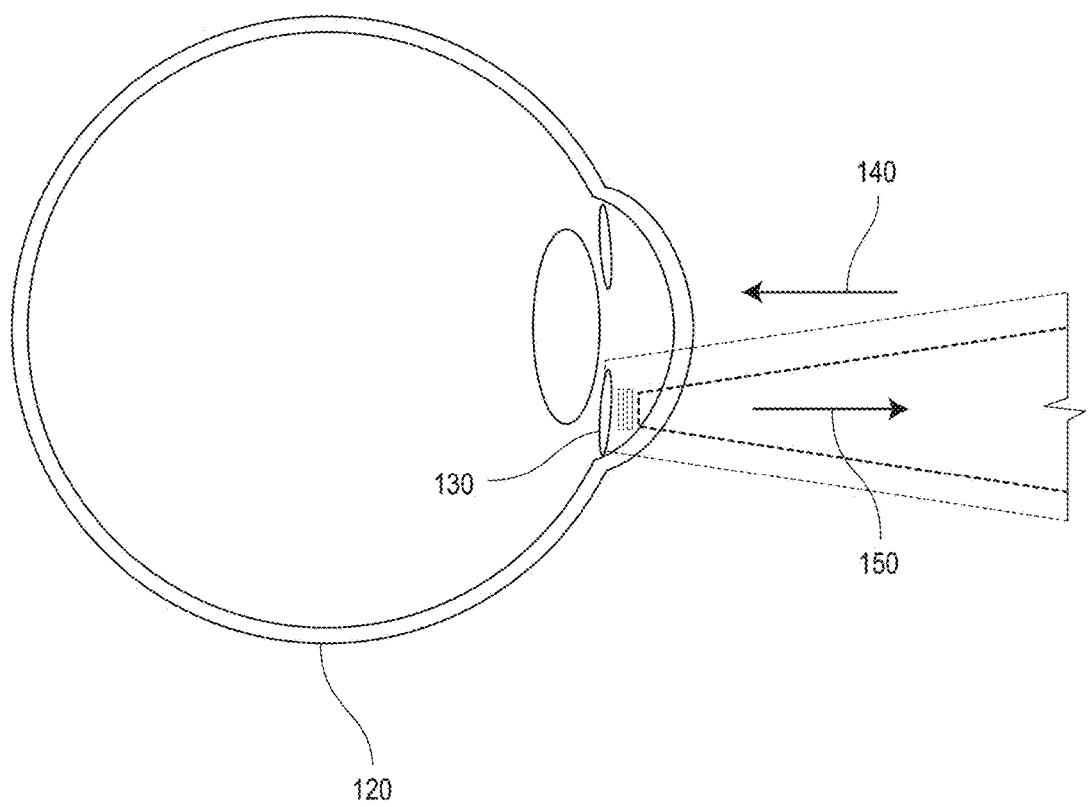
FIG. 1B is a close-up schematic diagram of the system for sensing intraocular pressure shown in FIG. 1A.

Referring now to the drawings, wherein like reference numerals designate identical or corresponding parts throughout the several views, FIGS. 1A and 1B are schematic diagrams of a system for sensing intraocular pressure in accordance with an embodiment of the invention. A battery-free IOP-sensing implant 130 with remote optical readout is inserted into the ocular anterior chamber of an eye 120, between the cornea and the iris. The sensor implant 130 is excited by an excitation beam 140 from an external light source built into a portable, handheld reader unit 110. The reader unit 110 scans the implant 130 over a range of wavelengths (e.g., from 750 nm to 1300 nm). The reflected light 150 from the implant 130 over the range of wavelengths is used to locate a dip in reflectance (i.e., a sudden decrease in reflectance). This dip in reflectance is then used to determine the current intraocular pressure ("IOP") inside the eye 120, as described further herein.

Figure 2A:
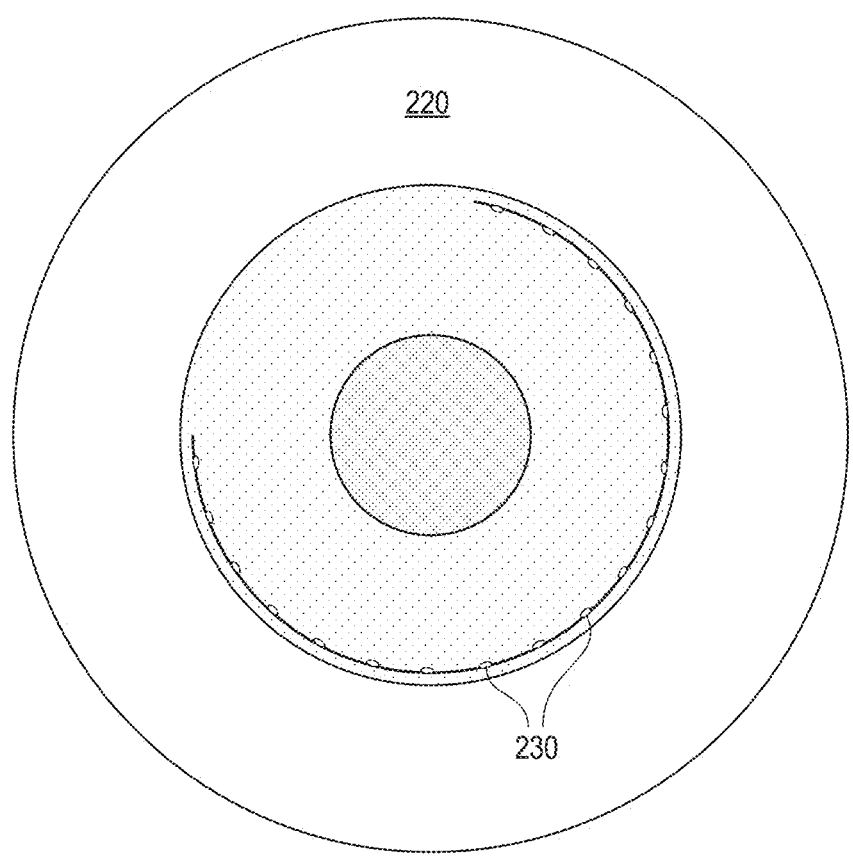
FIG. 2A is a front view of a system for sensing intraocular pressure in accordance with an embodiment of the invention.
Figure 2B:
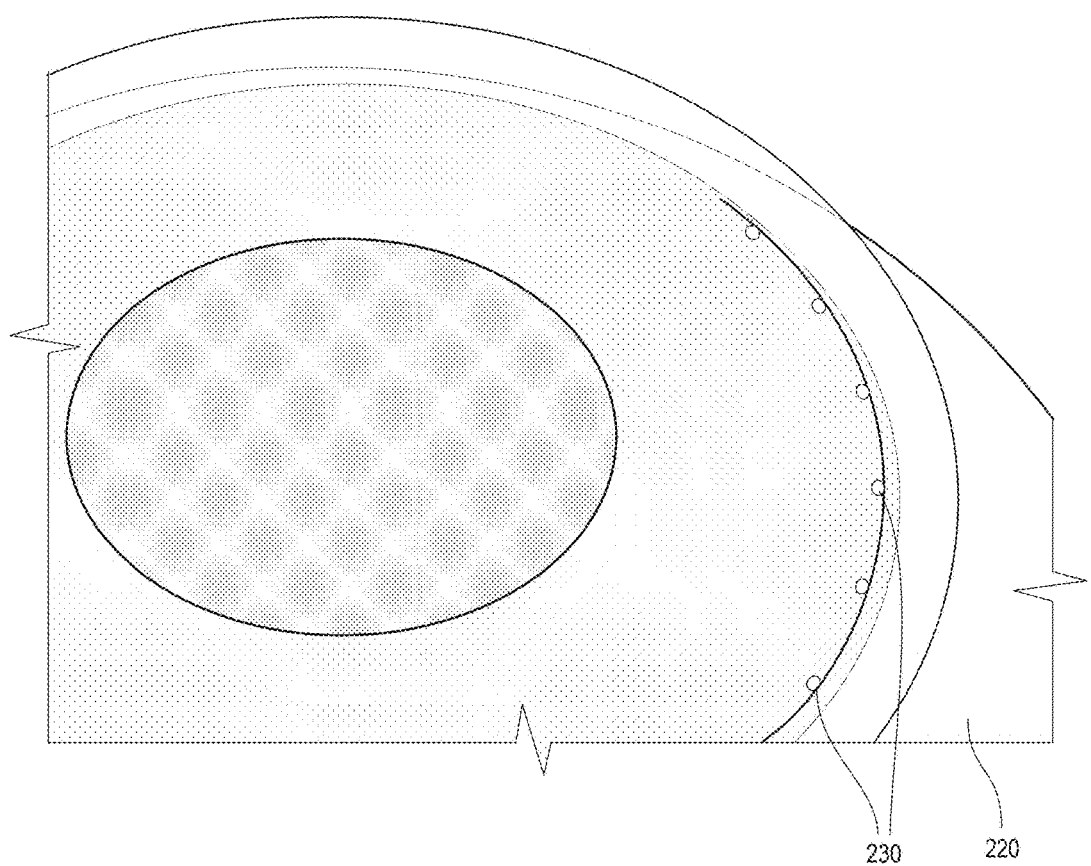
FIG. 2B is a perspective view of the system for sensing intraocular pressure shown in FIG. 2A.
Figure 2C:
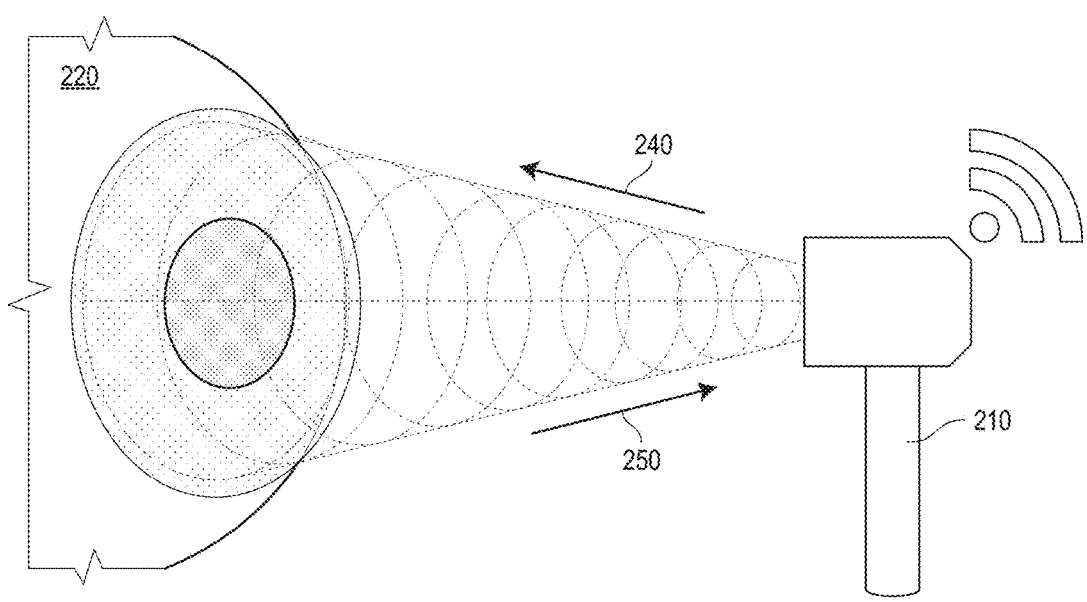
FIG. 2C is another perspective view of the system for sensing intraocular pressure shown in FIG. 2A.

FIGS. 2A-C are front and perspective views of a system for sensing intraocular pressure in accordance with an embodiment of the invention. In this embodiment, a plurality of battery-free IOP sensing implants 230 with remote optical readout are inserted into the ocular anterior chamber of an eye 220, between the cornea and the iris. The sensor implants 230 are excited by an excitation beam 240 from an external light source built into a portable, handheld reader unit 210. The reflected light 250 from the implants 230 contain information on the current IOP inside the eye 220.

Figure 2D:
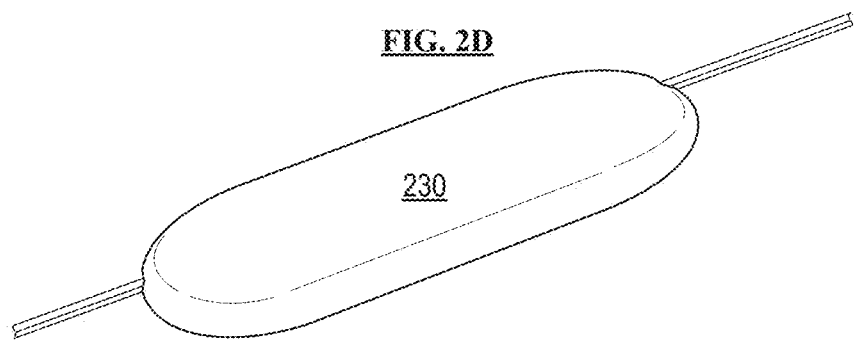
FIG. 2D is a close-up perspective view of the system for sensing intraocular pressure shown in FIG. 2A.
Figure 2E:
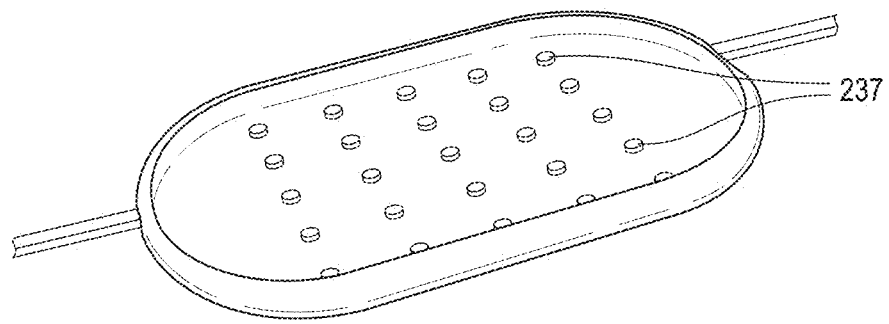
FIG. 2E is a close-up perspective cutaway view of the system for sensing intraocular pressure shown in FIG. 2A.

FIG. 2D is a close-up perspective view of an implant 230. FIG. 2E is a close-up perspective cutaway view of the implant 230 embedded with a plurality of nanophotonic components 237, described in further detail herein. Nanophotonic components 237 may comprise gold in one embodiment, such that nanophotonic components 237 are gold nanospots. Although shown and described as having a circular or cylindrical shape, it is contemplated that nanophotonic components 237 may take on any shape, such as triangles or squares. Further, although illustrated as opaque in FIGS. 2A-E, it is contemplated that implants 230 are optically transparent in the range of sensing wavelengths.

Figure 3A:
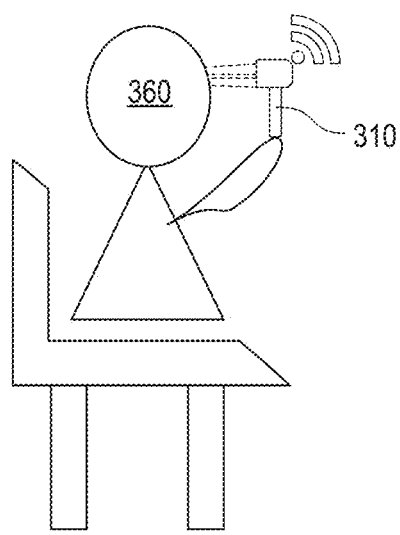
FIGS. 3A-3E are schematic diagrams of systems for sensing intraocular pressure in accordance with embodiments of the invention.
Figure 3B:
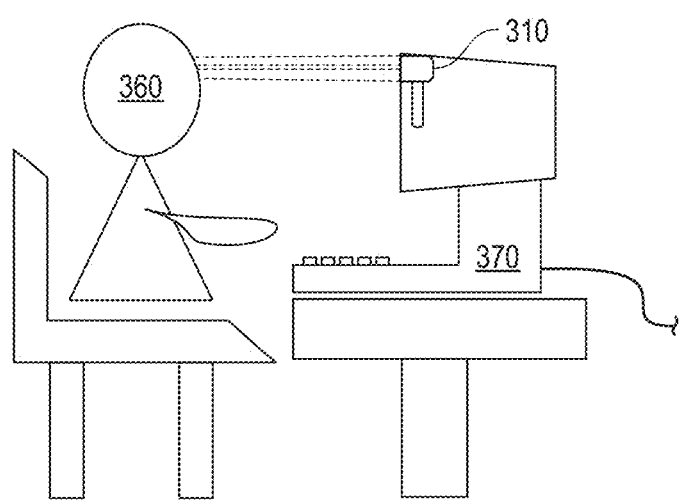
Figure 3C:
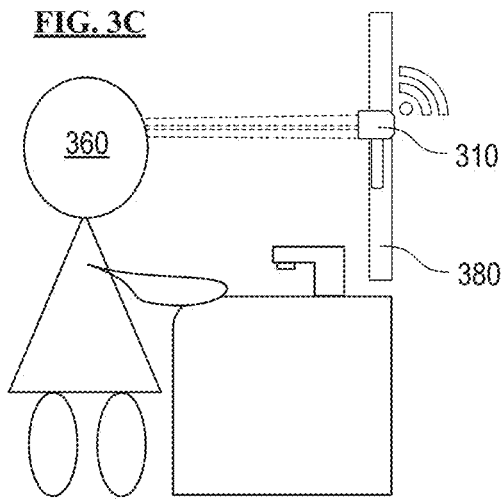
Figure 3D:
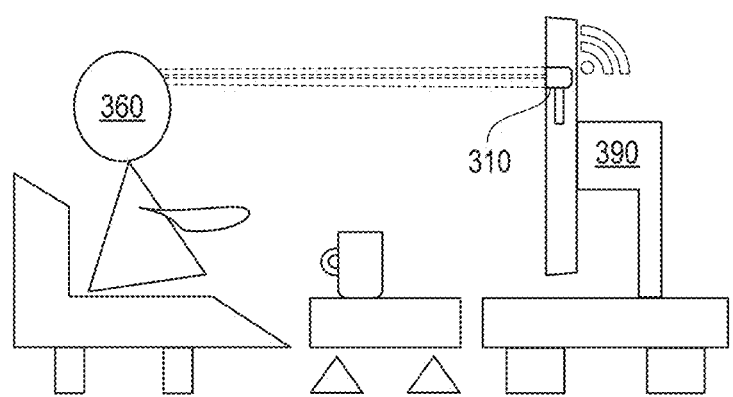

FIGS. 3A-E are schematic diagrams illustrating various IOP-sensing configurations that can be established using IOP sensing implants and readers 310 at home, hospitals, research labs and animal facilities with easy optical readout according to embodiments of the invention. FIG. 3A shows a user 360 using a reader unit 210 in handheld mode. FIG. 3B shows the reader unit 310 scanning an implant while the user 360 uses computer 370. FIG. 3C shows the reader unit 310 scanning an implant while the user 360 is in the bathroom near mirror 380. FIG. 3D shows the reader unit 310 scanning an implant while the user 360 is watching television 390.

Figure 3E:
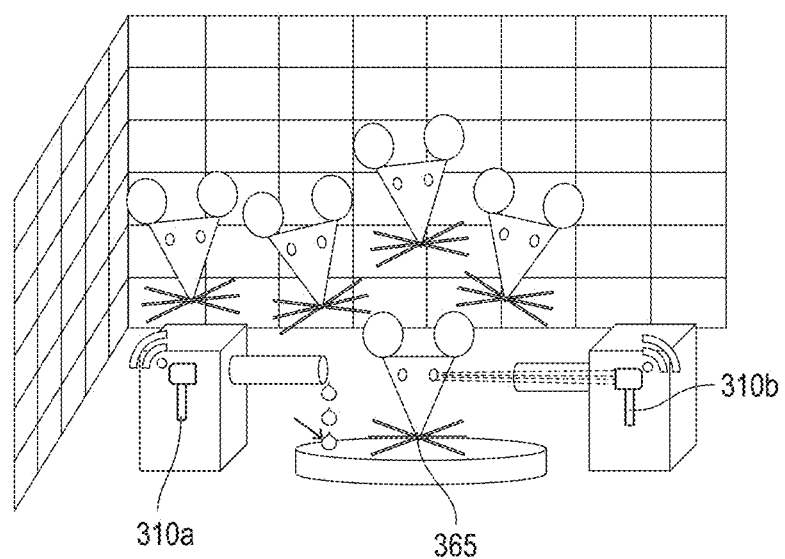

FIG. 3E shows the systematic tracking of the IOP of a research mouse 365 by a plurality of reader units 310a and 310b. The position and orientation of the head of mice are very predictable, and thus suitable for IOP sensing by reader units 310a and 310b when consuming water or food. In one embodiment, the collected IOP data is matched with the specific animal sensed (in this case, mouse 365) through the use of implanted electronic ID tags. Thus, a single IOP detection device (such as reader unit 310b) can be used to monitor a whole group of animals.

Figure 4A:
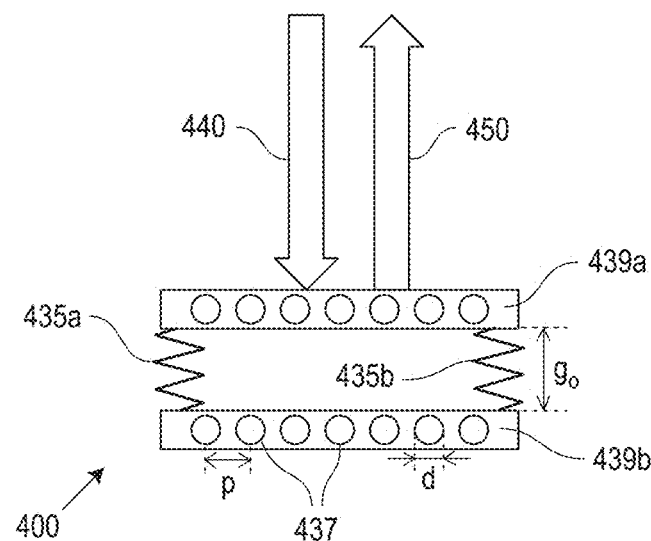
FIG. 4A illustrates pressure-sensitive bilayer-membrane disks at a first pressure according to an embodiment of the invention.
Figure 4B:
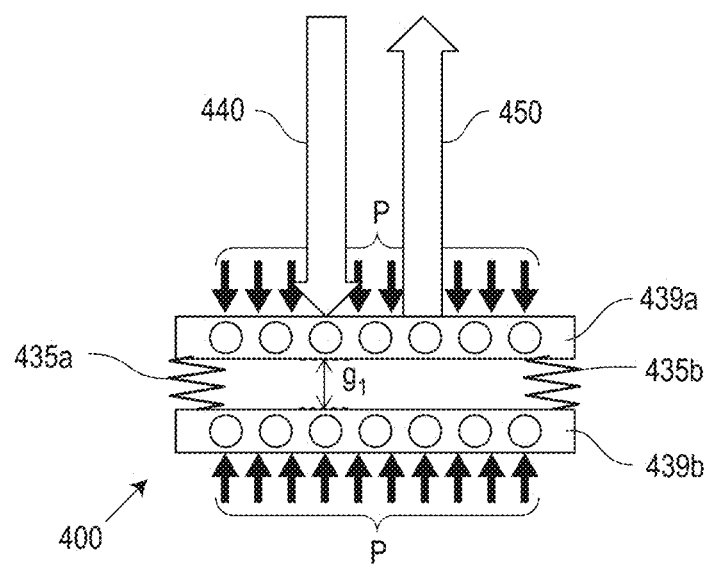
FIG. 4B illustrates pressure-sensitive bilayer-membrane disks at a second pressure according to an embodiment of the invention.

FIGS. 4A-B illustrate a small-scale, implantable pressure sensor 400 according to an embodiment of the invention. The sensor 400 comprises two pressure-responding flexible mechanical structures, in this case pressure-sensitive bilayer membrane disks 439a, 439b, embedded with a plurality of nanophotonic components 437 whose reflection spectrum varies as the geometry of the hosting structure changes in a predictable way as a function of IOP. Nanophotonic components 437 may be nanoparticles and/or nano-patterns having a pitch p and diameter d.

In this embodiment, force-resisting mechanical flexures 435a and 435b (e.g., springs) are used simply to represent the spring constant $k_y$ of membrane disks 439a, 439b, and no flexures 435a and 435b are actually physically present. Because membrane disks 439a, 439b comprise flexible and/or deformable materials, actual, physical flexures 435a and 435b are not necessary to realize a spring constant $k_y$. However, in other embodiments, it is contemplated that rigid membranes may be implemented as membrane disks 439a, 439b, and that force-resisting mechanical flexures 435a, 435b (of any material having a spring constant $k_y$) can be physically present in order to separate the membranes and provide the appropriate change in gap, and described further herein.

The initial intermembrane gap $g_o$ narrows to a second intermembrane gap $g_1$ as the ambient pressure P increases. Reference numeral 440 represents the light incident on the surface of membrane 439a. As the gap g becomes smaller, the resonance of the nanophotonic structures on the membrane shifts (i.e., a reflectance dip), changing the optical spectrum of the beam 450 that reflects off its surface. In other words, a change in intraocular pressure leads to a change in membrane deformation, causing a change in the gap size. The change in gap size, in turn, causes a shift in resonance (i.e., reflectance dip). By using a previously obtained relationship between intraocular pressure and resonance shift, an accurate IOP reading can be made with the shift in resonance dip.

Figure 4C:
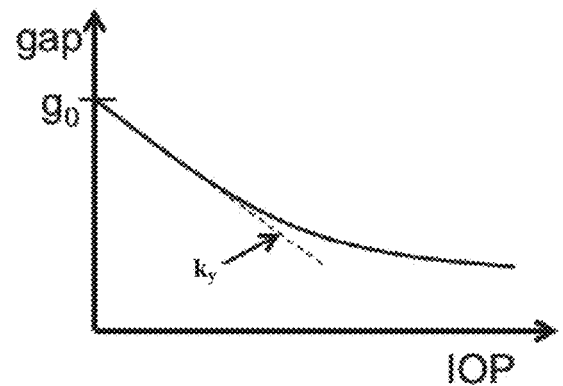
FIG. 4C is a graph illustrating the relationship between IOP and the gap between the pressure-sensitive bilayer-membrane disks illustrated in FIGS. 4A and 4B.
Figure 4D:
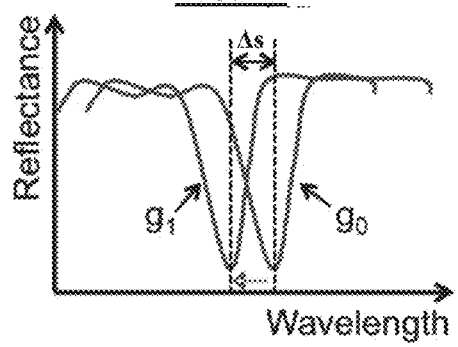
FIG. 4D is a graph illustrating the relationship between resonance wavelength and reflectance of the nanoparticles of the pressure-sensitive bilayer-membrane disks illustrated in FIGS. 4A and 4B.
Figure 4E:
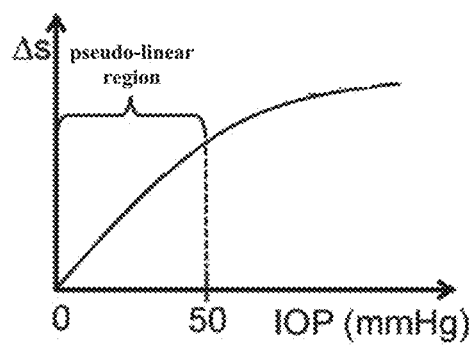
FIG. 4E is a graph illustrating the relationship between IOP and the shift in reflectance of the nanoparticles of the pressure-sensitive bilayer-membrane disks illustrated in FIGS. 4A and 4B.

FIG. 4C is a graph illustrating the relationship between IOP and the gap between the pressure-sensitive bilayer-membrane disks 439a, 439b illustrated in FIGS. 4A and 4B. FIG. 4D is a graph illustrating the relationship between wavelength of incidental light and reflectance of the nanophotonic components 437 of the pressure-sensitive bilayer-membrane disks 439a, 439b illustrated in FIGS. 4A and 4B. $\Delta s$ represents the shift of the resonance (i.e., the sudden decrease or dip in the reflectivity) caused by the change in gap from $g_o$ to $g_1$. FIG. 4E illustrates the shift of resonance, $\Delta s$, as a function of IOP. In the pseudo-linear region, an IOP reading can be easily and reliably obtained.

Figure 5A:
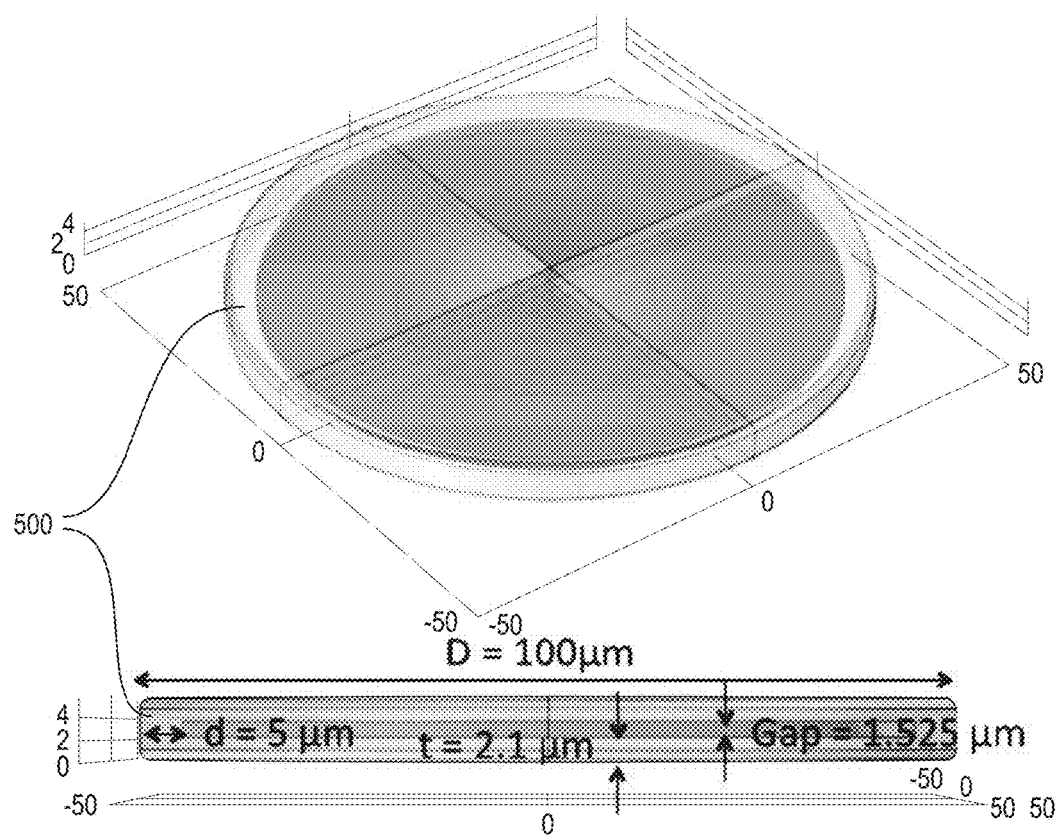
FIG. 5A illustrates COMSOL simulation results of a sealed Parylene-C bilayer-membrane disk according to an embodiment of the invention.

In one embodiment, simple, reliable mechanical designs and biocompatible materials are used in the disclosed systems for sensing IOP. For example, a Parylene-C bilayer membrane disk 500 can be used, as shown in FIG. 5A. Although shown and described with respect to a Parylene-C bilayer membrane disk, however, it is contemplated that several other materials and techniques may be used to transform the IOP change into predictable mechanical deformation. FIG. 5A illustrates exemplary dimensions of a Parylene-C bilayer membrane disk 500 (diameter=100 µm; thickness=2.1 µm; initial gap=1.525 µm). However, it is contemplated that other dimensions may be used to achieve similar results.

Figure 5C:
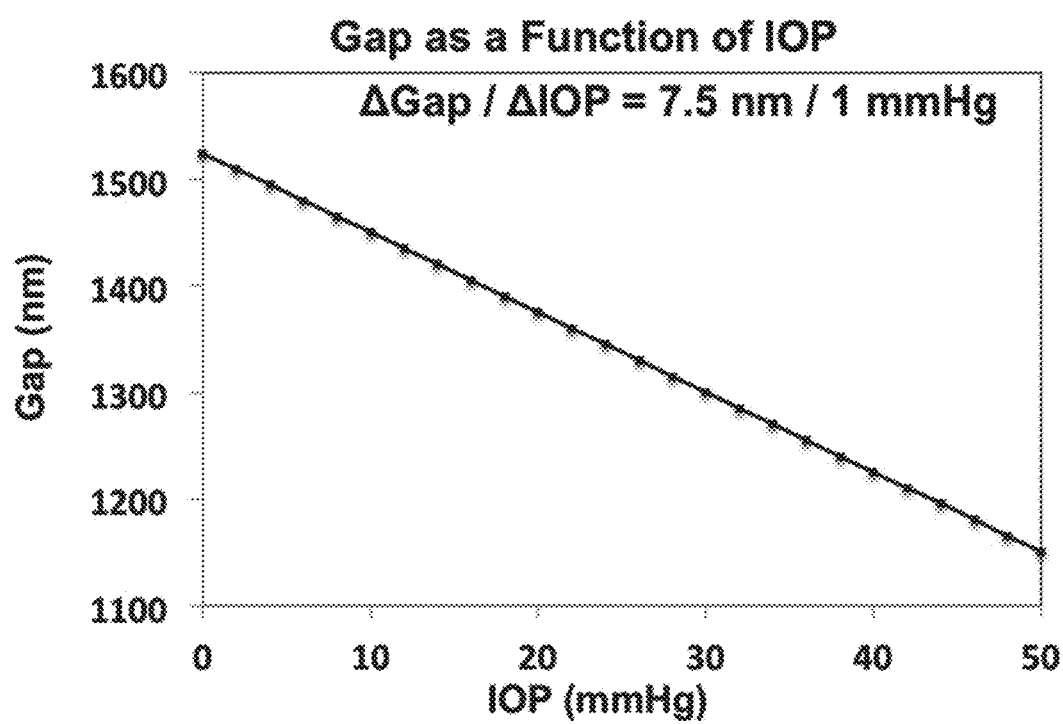
FIG. 5C is a graph illustrating the relationship between IOP and the intermembrane gap according to an embodiment of the invention.

Finite element method (FEM) simulation results are shown in FIGS. 5B and 5C showing the deformation properties of the Parylene-C bilayer membrane disk 500. FIG. 5B illustrates the maximum intended deformation of the membranes of the Parylene-C bilayer membrane disk 500. As shown in FIG. 5C, the gap between the membranes varies linearly as a function of IOP between 1525 nm (at 0 mmHg) and 1150 nm (at 50 mmHg), at a rate of −7.5 nm/mmHg. As understood by one skilled in the art, the design parameters of the Parylene-C bilayer membrane disk 500 can be modified to make the membrane disk 500 more or less sensitive (e.g., 50 nm/mmHg or 1 nm/mmHg) to environmental pressure changes.

Figure 6A:
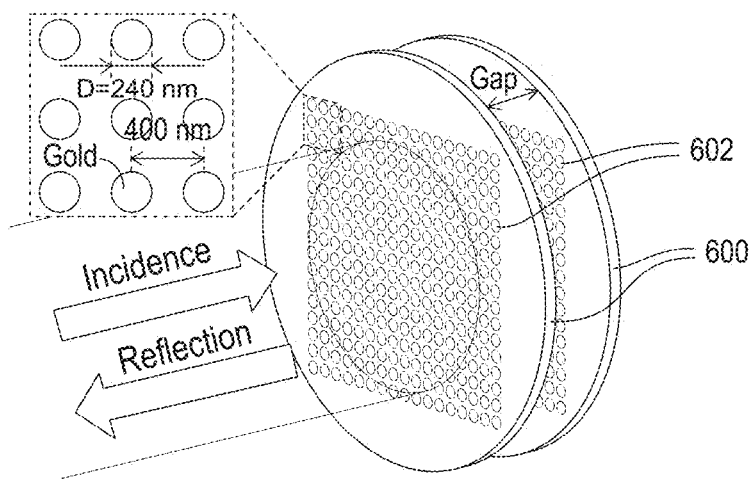
FIG. 6A is a schematic diagram illustrating a Parylene-C bilayer-membrane disk embedded with gold nanospot arrays according to an embodiment of the invention.

Any nanophotonic structures may be implanted into the Parylene-C bilayer membrane disk 500 (or other suitable bilayer membrane disk). For example, as shown in FIG. 6A, high-Q nanospot arrays 602 may be embedded into a Parylene-C bilayer membrane disk 600. In this example, nanospot arrays 602 comprise gold. It is contemplated, however, that nanospot arrays 602 may alternatively or additionally comprise any number of other suitable materials, such as silver, or other bio-compatible metals or dielectric materials with proper optical properties, i.e., refractive index; transmission, reflection, and/or absorption rates in the wavelength range of interest (750 nm to 1300 nm).

Figure 6B:
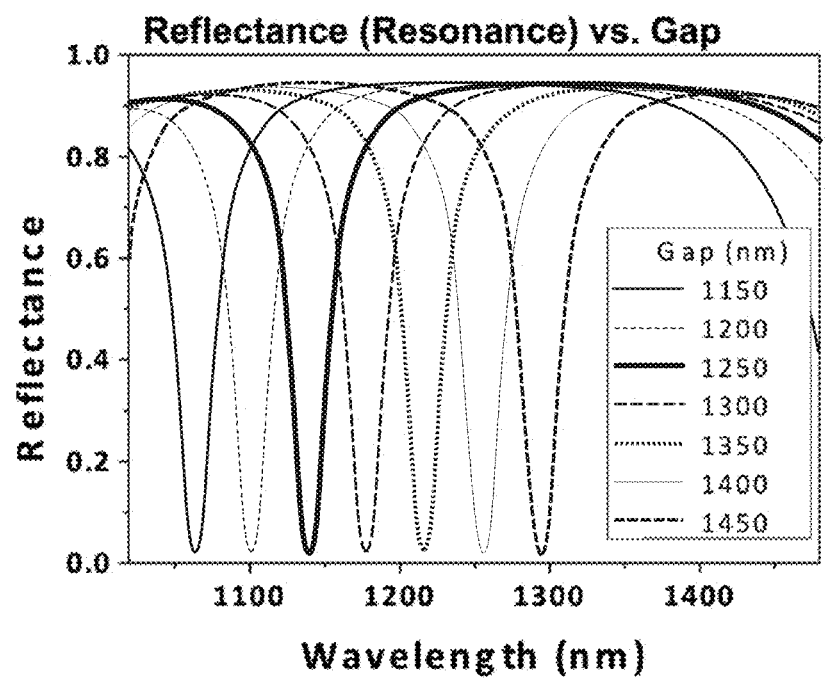
FIG. 6B is a graph illustrating the reflectance spectra of the Parylene-C bilayer-membrane disk illustrated in FIG. 6A as a function of the intermembrane gaps.

The diameter of the nanospots, the pitch of the array, the refractive indices of the membrane material and surrounding medium, and the gap between the membranes determine the resonance wavelength, resonance quality factor, free spectral range (FSR), and number of modes inside the FSR. As shown in FIG. 6B, as the gap decreases, the dip in the reflectance, which is caused by the resonance of the bilayer membranes embedded with the nanophotonic structures, shifts to lower wavelengths. Because the light absorption in the cornea and in aqueous humor starts to increase rapidly for light above 1300 nm, the most useful optical window according to embodiments of the invention exists between 750 nm and 1300 nm.

Figure 6C:
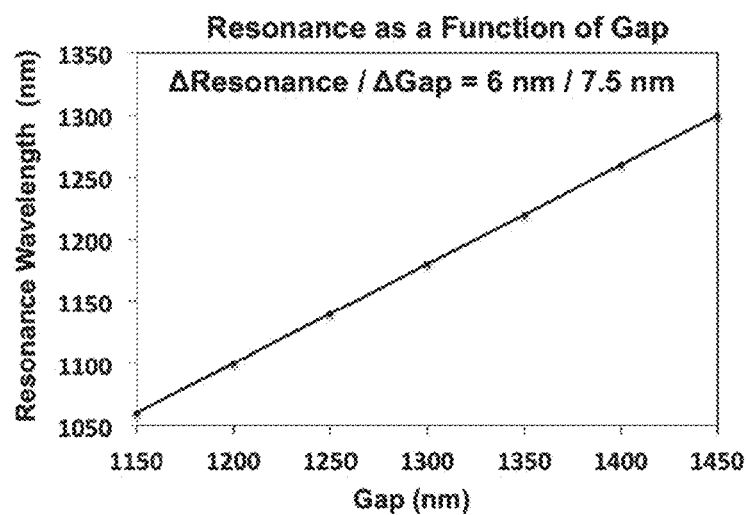
FIG. 6C is a graph illustrating the shift in resonance of the Parylene-C bilayer-membrane disk illustrated in FIG. 6A as a function of the intermembrane gaps.
Figure 6D:
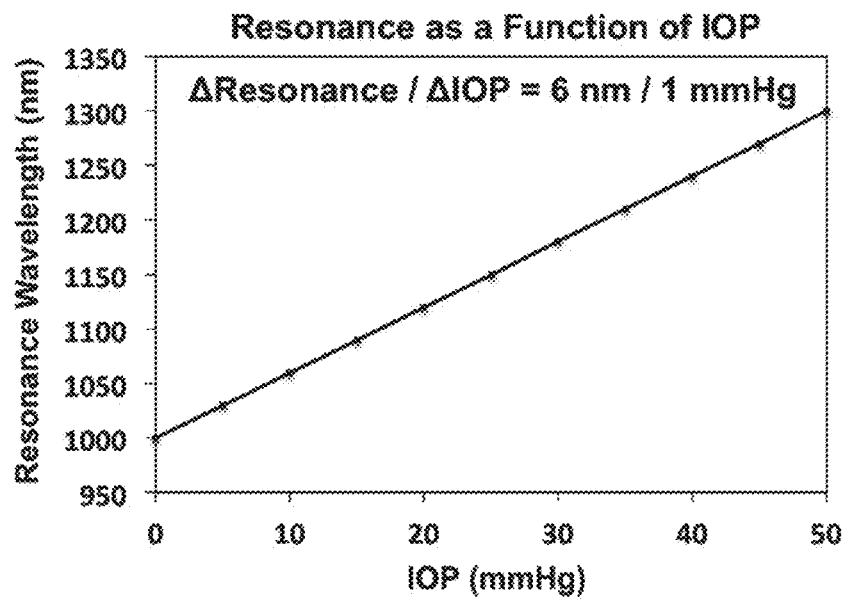
FIG. 6D is a graph illustrating the shift in resonance of the Parylene-C bilayer-membrane disk illustrated in FIG. 6A as a function of IOP.

Turning back to FIG. 6A, the spot diameter, array pitch, and intermembrane gap are 240 nm, 400 nm, and 1.525 µm, respectively. With these design parameters, when the gap decreases from 1450 nm to 1150 nm due to increasing IOP, the resonance (i.e., the dip in the reflectance) shifts from about 1300 nm to above 1060 nm, as shown in FIGS. 6B and 6C. This is equivalent to about a 240 nm shift over a 40-mmHg change (i.e., from 10 mmHg to 50 mmHg), or a rate of 6 nm/mmHg, as shown in FIG. 6D. A 6-nm shift of a sharp, high-Q resonance dip can be resolved using commercial miniature spectrometers or detected by using a photodiode after converting the wavelength shift to the intensity change based on interferometric techniques. The final mapping between resonance shift and IOP as shown in FIG. 6D is linear.

A number of advantages can be realized by using the disclosed nanophotonic approach. For example, the disclosed implant has a simple, small structure that can be easily fabricated. Compared to an optical technique that relies purely on the interference between the two dielectric surfaces, the addition of nanophotonic components doubles the quality factor of the resonance dip in the reflectance spectrum and achieves larger than 90% swings in reflectivity at resonance. In addition, within a circular area with a diameter of 100 µm on the membrane, an array of approximately 8,000 nanophotonic components can be fit due to their extremely small, nanoscale dimensions. This high packing density enables the 100 µm diameter implant to generate strong reflective optical signals that can be detected from a remote distance over 20 cm.

FIG. 7 is a schematic diagram of an on-bench characterization chamber 700 for characterizing a system for sensing intraocular pressure according to an embodiment of the invention. The chamber 700 simulates an ocular environment in which the disclosed IOP sensors may be used and tested to optimize performance. The chamber 700 includes saline solution 711; flow regulator 713 for regulating the flow of saline solution 711; valve 714 for controlling the access of saline solution 711 to pressure chamber 716; gas 723; pressure regulator 721 for regulating the pressure of gas 723; and valve 718 for controlling access of gas 723 to pressure chamber 716.

The chamber 700 simulates the environment of the anterior chambers of human/rodent eyes, allowing the testing of the sensors in air as well as saline solution. The following tests and observations can be performed or made using the chamber 700: optical resonant frequency and quality (Q) factor of the nanophotonic array; vertical mechanical resonant frequency and Q factor of the bilayer-membrane disk; the membrane's mechanical responsivity at heartbeat frequencies; pressure sensitivity, responsivity, and drift; temperature influence; dependence of remote readout distance on sensor size and distance; and observation on biological medium (viscosity) effect. These outcomes and findings can be used to optimize performance of the disclosed IOP sensors in one embodiment.

In the past decade, large NIH-sponsored clinical trials have established that tight IOP control leads to better clinical outcome. In addition, it has been proposed that diurnal variations in IOP are important for the optimal management of disease. Because IOP can be monitored frequently during the course of a day according to embodiments of the invention, the readings can be stored for analysis and used to prompt patients to adhere to medications and to notify the physician about suboptimal IOP control. The disclosed sensors can also serve as a sensing arm for drug dosing, much like the use of glucose sensors to inform diabetic patients of the needed medication. As non-compliance to medication is known to be a major factor in treatment failure, convenient home monitoring of IOP will improve patient compliance with medication and treatment outcomes. More accurate IOP profiles from individual patients also allow for the development of tailored medication protocols for individual patients to increase clinical efficacy. In addition, the disclosed embodiments will provide doctors with more detailed IOP tracking to understand the relationship of IOP to disease in a given patient, and to use this information for improved clinical management. Given its highly miniaturized form, IOP sensors according to embodiments of the invention can be used not only in humans, but also to record IOPs automatically from research animal colonies, thus assisting in the development of new drugs for glaucoma therapy.

The present invention has been described in relation to particular examples, which are intended in all respects to be illustrative rather than restrictive. Those skilled in the art will appreciate that many different combinations of materials and components will be suitable for practicing the present invention. For example, although shown and described with respect to sensing intraocular pressure, it is contemplated that the present invention can be modified to sense pressure at any location within or outside of the body.

Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A system for sensing biological pressure, comprising:
an implantable device comprising a first membrane structure, a second membrane structure, and a plurality of nanophotonic components adapted to reflect light, wherein the first and second membrane structures are separated by a gap and the first membrane structure is movable with respect to the second membrane structure in response to a change in ambient pressure such that the implantable device has a resonance wavelength that shifts as a size of the gap changes; and a reader unit adapted to transmit optical light to the implantable device and detect the resonance wavelength of the implantable device based on light reflected from the implantable device.

2. The system of claim 1, wherein the reader unit is adapted to detect the resonance wavelength based on a shift in the resonance wavelength of light reflected from the implantable device.

3. The system of claim 2, wherein the reader unit is adapted to determine the biological pressure based on the detected resonance wavelength of the implantable device.

4. The system of claim 1, wherein the implantable device is adapted for implantation into an eye, and wherein the biological pressure is an intraocular pressure.

5. The system of claim 1, wherein the first and second membrane structures are both deformable in response to the change in ambient pressure.

6. The system of claim 1, wherein the first and second membrane structures are separated by one or more mechanical flexures.

7. The system of claim 1, wherein the first and second membrane structures are rigid.

8. The system of claim 1, wherein the nanophotonic components are nanoparticles.

9. The system of claim 1, wherein the nanophotonic components are embedded in the first and second membrane structures.

10. The system of claim 1, wherein the implantable device is a first implantable device, the system further comprising a plurality of additional implantable devices, each additional implantable device having the same structure as the first implantable device.

11. The system of claim 10, wherein each implantable device is coupled to another implantable device.

12. An apparatus for sensing biological pressure, comprising:

an implantable device comprising a first membrane structure, a second membrane structure, and a plurality of nanophotonic components adapted to reflect light, wherein the first and second membrane structures are separated by a gap and the first membrane structure is movable with respect to the second membrane structure in response to a change in ambient pressure such that the implantable device has a resonance wavelength that shifts as a size of the gap changes, the resonance wavelength being detectable based on light reflected by the implantable device.

13. The apparatus of claim 12, wherein the first and second membrane structures are separated by one or more mechanical flexures.

14. The apparatus of claim 12, wherein the first and second membrane structures are rigid.

15. The apparatus of claim 12, wherein the nanophotonic components are nanoparticles.

16. The apparatus of claim 12, wherein the nanophotonic components are embedded in the first and second membrane structures.

17. The apparatus of claim 12, wherein the implantable device is a first implantable device, the apparatus further comprising a plurality of additional implantable devices, each additional implantable device having the same structure as the first implantable device.

18. The apparatus of claim 17, wherein each implantable device is coupled to another implantable device.

19. The apparatus of claim 12, further comprising a reader unit adapted to detect the resonance wavelength of the implantable device.

20. The apparatus of claim 19, wherein the reader unit is adapted to detect the resonance wavelength based on a shift in the resonance wavelength of light reflected by the implantable device.

21. The apparatus of claim 20, wherein the reader unit is adapted to determine the biological pressure based on the detected resonance wavelength of the implantable device.

22. The apparatus of claim 12, further comprising a reader unit adapted to detect the resonance wavelength of the implantable device, the reader unit adapted to transmit a plurality of wavelengths to the implantable device, and detect the resonance wavelength based on a reflected plurality of wavelengths of light reflected by the implantable device.

23. The apparatus of claim 22, wherein the reader unit is adapted to determine the biological pressure based on the detected resonance wavelength of the implantable device.

24. The apparatus of claim 12, wherein the implantable device is adapted for implantation into an eye, and wherein the biological pressure is an intraocular pressure.

25. The apparatus of claim 12, wherein the first and second membrane structures are both deformable in response to the change in ambient pressure.

* * * * *